United States Patent [19]

Forni et al.

[11] 4,029,719

[45] June 14, 1977

[54] PROCESS FOR THE DIMERIZATION OR CO-DIMERIZATION OF LINEAR OLEFINS AND CATALYSTS THEREFORE

[75] Inventors: Lucio Forni; Renzo Invernizzi, both of Milan, Italy

[73] Assignee: Societa' Italiana Resine S.I.R. S.p.A., Milan, Italy

[22] Filed: Dec. 8, 1975

[21] Appl. No.: 638,387

Related U.S. Application Data

[62] Division of Ser. No. 398,507, Sept. 18, 1973, abandoned.

[30] Foreign Application Priority Data

Sept. 20, 1972 Italy ........................... 29427/72

[52] U.S. Cl. ........................... 260/683.15 R
[51] Int. Cl.² ........................... C07C 3/20
[58] Field of Search ........................... 260/683.15 R

[56] References Cited

UNITED STATES PATENTS

| | | | |
|---|---|---|---|
| 3,325,465 | 6/1967 | Jones et al. | 260/683.15 R |
| 3,341,620 | 9/1967 | Clark et al. | 260/683.15 R |

Primary Examiner—C. Davis
Attorney, Agent, or Firm—Sughrue, Rothwell, Mion, Zinn & Macpeak

[57] ABSTRACT

Process for the preparation of catalysts suitable for the production of linear olefins by dimerization or co-dimerization of linear olefins having small numbers of carbon atoms, characterized by depositing one or more metals chosen from among those belonging to group VIII of the periodic system of elements on a natural or synthetic crystalline zeolite by ion exchange to a quantity of deposited metal of from 0.1 to 50% by weight with respect to the zeolite itself, by bringing the resulting product into contact with an organic or inorganic base in the liquid or gaseous form at a temperature in the range from −35 to 250° C for a time of at least 30 minutes, and by eliminating the excess of the base and heat-treating at temperatures in the range from 50 to 450° for at least 30 minutes, and a process for the preparation of linear olefins having from 6 to 24 carbon atoms in the molecule, characterized by the introduction of one or more linear olefins having from 3 to 12 carbon atoms in the molecule to the catalysts obtained, and by operating at temperatures of from 130 to 260° C and at pressures of from 2 to 70 atmospheres.

12 Claims, No Drawings

PROCESS FOR THE DIMERIZATION OR CO-DIMERIZATION OF LINEAR OLEFINS AND CATALYSTS THEREFORE

This is a division of application Ser. No. 398,507, filed Sept. 18, 1973, and now abandoned.

The present invention relates to a process for the preparation of linear olefins by dimerization or co-dimerization of linear olefins having low numbers of carbon atoms. In particular, the invention relates to the preparation of linear olefins having from 6 to 24 carbon atoms in the molecule by dimerization or co-dimerization of linear olefins having from 2 to 12 carbon atoms in the molecules. The invention also relates to a particularly active and selective catalyst for the said dimerization or co-dimerization reaction.

The linear olefins having from 6 to 24 carbon atoms in the molecule are widely used in industry. These olefins can be used for example for the alkylation of benzene in the production of alkylbenzenes having linear paraffinic chains, or they can be converted into alcohols by hydration or hydroformylation processes. The said alkylbenzenes and the said alcohols are valuable intermediates for the synthesis of biodegradable detergents, such as alkylbenzenesulfonates and alkylsulfates.

Various processes are known in the art for the production of linear olefins by dimerization or co-dimerization of olefins having low numbers of carbon atoms. According to the said known processes, an olefin or a mixture of several olefins is brought into contact, in a reaction zone, with a catalyst consisting of metal oxides deposited on a support. The reaction is carried out at high temperatures and pressures.

Supports suitable for the purpose are coke, active charcoal, animal charcoal, and silica, this last being used alone or in combination with oxides of boron, zirconium, magnesium, and aluminium. The metal oxide catalysts normally used are those of cobalt, copper, and nickel. However, the catalysts of prior art do not give completely satisfactory results in the dimerization or co-dimerization of olefins, mainly because of the low values of selectivity for the formation of the linear olefins. One thus obtains reaction products that are highly contaminated above all by the presence of branched olefins, with the result that costly processes are required for the separation and purification of the useful fraction. It has now been found that the described disadvantages can be eliminated or at least greatly reduced by dimerization or co-dimerization of the olefins at elevated temperatures and pressures with novel catalysts.

One object of the present invention is therefore an improved process for the dimerization or co-dimerization of linear olefins having low numbers of carbon atoms. Another object of the present invention is catalysts that are highly active and selective in processes for the preparation of linear olefins by dimerization or co-dimerization of linear olefins having low numbers of carbon atoms.

A further object of the present invention is the process for the preparation of the said catalysts.

Other objects of the invention will appear from the following description. It has now been found that linear olefins having from 6 to 24 carbon atoms in the molecule can be produced according to the invention process which is characterized by contacting one or more linear olefins having from 3 to 12 carbon atoms in the molecule with a catalyst obtained by activating, by means of an organic or inorganic base, a crystalline zeolite on which has previously been deposited at least one metal selected from the group VII of the periodic system of elements, and operating at temperatures of from about 130° to 260° C and at pressures of from about 2 to 70 atmospheres.

The linear olefins produced according to the present invention contain from 6 to 24 carbon atoms per molecule. Specific examples of the products are hexene, heptene, octene, nonene, dodecene, and hexadecene. For this purpose linear olefins having from 3 to 12 carbon atoms in the molecule, such as propylene, butene, hexene, octene, and dodecene, are fed to the catalyst. The feed olefins having 4 or more carbon atoms will preferably have their unsaturation in the $\alpha$-position, but olefins with internal unsaturation can also be used for the purpose of the present invention. A single olefin or a mixture of 2 or more olefins may be fed to the catalyst. When two or more olefins are present, the reaction of dimerization or that of co-dimerization is observed.

The dimerization is normaly carried out at temperatures of from about 130° to 260° and at pressures of from about 2 to 70 kg/cm$^2$, the olefin being fed to the catalyst in the form of a stationary bed. The preferred values for the temperature are those in the range from 150° to 190° C, while the preferred values for the pressure vary from 20 to 60, especially from 30 to 50 kg/cm$^2$. The feed rates are generally maintained in the range of values from 0.1 to 20 volumes of liquid olefin per volume of the catalyst per hour. The conditions will obviously vary for each particular olefin fed in, but always remain within the ranges of values defined above. Typically, in the case of the dimerization of 1-butene to linear octene, the best results are obtained by operating at rates of between 0.1 and 20 volumes of liquid 1-butene per volume of catalyst per hour at pressures of from 30 to 50 kg/cm$^2$ and at temperatures of from 150° to 190° C.

In each case, by dimerization or co-dimerization with the catalysts of the present invention and in the range of conditions defined above, one obtains a conversion equal to or greater than 40% with respect to the feed olefins, the selectivity for linear olefins with respect to the fraction converted being equal to greater than 70%.

The catalysts of the present invention consist of the products obtained by activation of a crystalline zeolite on which at least one metal chosen from among those of group VIII of the periodic system of elements has previously been deposited. In the course of the following description, therefore, the products that are obtained by deposition of one or more metals of group VIII on a crystalline zeolite by ion exchange will be referred to as "catalyst precursors".

These precursors have low activities and selectivities in the dimerization of olefins. Catalysts, on the other hand, are to be understood as the products that are obtained from the said precursors by the special activation process of the invention that will be described later. These catalysts exhibit high activity and selectivity characteristics in the processes for the production of linear olefins by dimerization of olefins having low numbers of carbon atoms. The crystalline zeolites that can be used in the present invention include both the natural zeolites and the synthetic zeolites, the latter being commonly known as molecular sieves; (see Ch.

K. Hersch, Molecular Sieves, Reinhold Publ., New York 1961). The natural zeolites are for example those described in Kirk-Othmer, "Encyclopedia of Chemical Technology", first edition, volume 12, pages 295 et seq.; information on the composition of synthetic zeolites and a process for their preparation can be found for example in U.S. Pat. No. 2,972,643. The natural and synthetic zeolites vary considerably in their composition, but generally contain silicon, aluminum, oxygen, and one or more elements belonging to the alkali or alkaline earth metals.

In the preparation of the catalyst precursors of the present invention are used those zeolites containing silicon, aluminum, oxygen, and one or more elements belonging to the alkali or alkaline earth metals that have a specific surface area of from about 200 to 1200 $m^2/g$ and a pore diameter of from about 6 to 15 A. The preferred crystalline zeolites are those that contain silicon, aluminium, and oxygen and one or more elements chosen from among sodium, potassium, calcium, and magnesium and that have a specific surface area in the range of values defined above and a pore diameter of from about 8 to 13 A.

The metals of group VIII that can be used for the purposes of the present invention are those included in the said group of the periodic system of elements, i. e. iron, cobalt, nickel, ruthenium, rhodium, palladium, osmium, iridium, and platinum. Among these elements cobalt and nickel are preferred, and between these, nickel is absolutely preferred.

In the preparation of the catalyst precursors of the present invention, the catalytic metals are deposited on the zeolite by an ion-exchange process. More particularly, the zeolite particles, after grinding and sieving to obtain the desired particle size composition, are brought into contact with an aqueous solution containing the metal ions to be exchanged. The aqueous solution used for the purpose contains the transition metal salt in a range of values from about 0.1 to 80% by weight, the preferred values being from 1 to 10% by weight. The salts of the transition metal preferably used for the purpose are those that are soluble in water or in alcohol, such as nitrates, chlorides, sulphates, acetates, citrates, oxalates, arsenites, carbonates, chromates, molybdates, sulphites, and soluble organic salts such as butanoates, pentanoates, and hexanoates. Moreover, the ionexchange reaction between the transition-metal ion and the alkali metal or alkaline earth metal ions present in the crystalline zeolite may be carried out at any temperatures in the range of from about 0° to 100° C, though it is preferable to operate at temperatures of from 10° to 30° C. Moreover, during the ion-exchange reaction the pH of the solution is maintained at controlled and constant values between about 5 and 6, the best results being obtained at pH values of from 5.3 to 5.7.

In the preparation of the catalyst precursor in accordance with the present invention, any known technique may be used for the contact between liquids and solids. For example, it is possible to allow the aqueous solution of the transition metal salts to percolate through particles of the zeolite, or the zeolite may be suspended in the solution itself. In each case, the conditions must be adjusted so that, at the end of the treatment, the quantity of the transition metal is in the range of values from about 0.1 to 50% by weight with respect to the zeolite and preferably from 1 to 20% by weight. After the ion exchange, the solid is separated from the solution and washed repeatedly with deionized water. The washing operations are continued until the anion of the salt used has practically completely disappeared from the wash water. Finally, the catalyst precursor obtained in this way is subjected to drying, operating at temperatures below about 120° C for a time of at least about 30 min.

The catalysts of the present invention are obtained by activating the corresponding precursors in order to confer high activity and selectivity in the dimerization of olefins. This activation treatment consists essentially in bringing the catalyst precursor into contact with an organic or inorganic base and then eliminating the excess of the base from the catalyst obtained in this way. Among the inorganic bases, ammonia has been found to be useful for the purpose, while among organic bases, the aliphatic amines such as monomethylamine, diethylamine, butylamine, and ethylenediamine and the aromatic bases such as pyridine, piperidine, picoline, quinoline, and isoquinoline are preferred. According to the present invention, the catalyst precursor is brought into contact with the organic or inorganic base, the latter being in the liquid or gaseous form, and the operation being carried out at temperatures of from about −35° to 250° C.

Any method known in the art for contact between liquids and solids or between gases and solids may be used for the purpose. Thus, the catalyst precursor may be suspended in the liquid base, or the said base may be allowed to percolate through a bed of particles of the precursor. However, in the preferred form, a gaseous stream of ammonia or of an organic base is passed through the particles of the precursor. In this case the gaseous stream may also contain an inert gas such as nitrogen. In the operation of activation with gas-solid contact, the preferred temperatures are those slightly above the boiling point of the chosen base, for example from 10° to 20° C above the said boiling point. In each case the treatment is continued for times of at lest about 30 min and preferably at least 3 hours. However, it is convenient to exceed times of about 5 hours, since no appreciable advantages are obtained in this way. It is noted that heat is evolved during the contact between the catalyst precursor and the base. In practice, therefore, the treatment should be continued at least until exothermicity is absent, i. e. until no further heat is developed. The activation of the present invention may obviously be carried out with a single organic or inorganic base or with several bases fed together or successively to the catalyst precursor.

At the end of the activation operation the excess base is eliminated from the catalyst at relatively low temperatures, generally below 250° C, and preferably in the range of values from about 0° to 100° C. For this purpose it is convenient to pass an inert gas, such as nitrogen, through the catalyst until the base disappears from the purge gas. Nitrogen is typically fed to the catalyst at a rate of 40 ml per minute per gram of the catalyst, for at least about half an hour and preferably for at least 3 hours.

Finally, a heat treatment is carried out on the catalyst obtained, by maintaining it at temperatures of from about 50° to 450° C, preferably from 150° to 350° C, for at least about 30 min and preferably for at least 1 hour, with constant maintenance of a stream of inert gas. In this treatment it is not convenient to exceed times of 3 hours, since no appreciable advantages are obtained.

The following experimental examples serve to illustrate the invention further, but without limiting it in any way.

EXAMPLE 1

In this experiment a synthetic zeolite containing silicon, aluminium, oxygen, and sodium, having a pore diameter of 10 A, and known commercially as Linde molecular sieve type 13 X, was used.

53 grams of this zeolite in the form of granules having dimensions of 40 to 60 mesh are treated with an aqueous solution containing 43.5 grams of nickel nitrate hexahydrate in 640 ml of de-ionized water. The process is carried out for about 50 hours at 25° C and with a pH of the solution of 5.5. After filtration and repeated washing with de-ionized water until nitrate ions have disappeared from the wash water, the solid is dried for 1 hour at 120° C. A catalyst precursor containing 5% by weight of nickel is obtained in this way.

6 grams of the precursor obtained in this way are placed in a glass column, into which 200 ml/min of anhydrous nitrogen saturated with n-butylamine vapour are allowed to flow at a temperature of 25° C. The process is carried out under these conditions for 3 hours. During the next 2 hours dry nitrogen is passed through the column at a rate of 200 ml/min. Finally, the temperature is raised to 250° C and the introduction of dry nitrogen at the said rate is continued for 1 hour. The catalyst obtained in this way was used for the dimerization of 1-butene.

More particularly, the experiment was carried out at 170° C at a pressure of 40 kg/cm$^2$, with introduction of 2 volumes of liquid 1-butene per volume of catalyst per hour. A conversion of 40.5% with respect to the butene fed in was obtained, with a selectivity for linear octene of 81.8%.

EXAMPLE 2

6 grams of the catalyst precursor obtained as described in the above example are treated with 200 ml/min of a gaseous stream comprising 90% by volume of dry nitrogen and 10% by volume of monomethylamine for 3 hours at a temperature of 25° C.

The subsequent treatment with nitrogen alone, first at a low temperature, and then at a high temperature, is the same as in the first example.

The dimerization of 1-butene, carried out under the conditions of the first example, gave a conversion of 79.2% and a selectivity for linear octene of 75.4%.

EXAMPLE 3

6 grams of the catalyst precursor obtained as decribed in the first example are treated with 200 ml/min of a gaseous stream comprising 80% by volume of dry nitrogen and 20% by volume of ammonia for 3 hours at a temperature of 25° C.

Subsequent treatment with nitrogen alone, first at a low temperature and then at a high temperature, is the same as in the first example.

The duration of 1-butene carried out under the conditions of the first example gave a conversion of 65% and a selectivity for linear octene of 72.7%.

EXAMPLE 4 (comparison)

6 grams of the catalyst precursor obtained as described in the first example are treated with nitrogen in the manner described in the foregoing examples, but in the absence of the base. The dimerization of 1-butene carried out under the conditions of the first example gave a conversion of 39.5%, with a selectivity for linear octene of 56%.

EXAMPLE 5 a. 6 grams of the catalyst precursor obtained as described in example 1 are heated for 2 hours in a stream of dry nitrogen to a temperature of 250° C.

b. 6 grams of the catalyst precursor obtained as described in example 1 are heated for 4 hours in a stream of dry nitrogen to a temperature of 700° C.

c. 6 grams of the catalyst precursor obtained as described in example 1 are activated with monomethylamine according to example 2.

With the catalyst obtained as described in a) to c) propylene is dimerized to hexene and octene-1 to hexadecene. The reaction conditions and the results are stated in Table I:

Table I

| Catalyst | Olefin | Olefin-charge rate, ml/h | reaction temp., ° C | pressure, kg/cm$^2$ | selectivity of the formation of the dimer[+] |
|---|---|---|---|---|---|
| a) | propylene | 13 | 175 | 70 | 43.7 |
| b) | propylene | 18 | 180 | 70 | 53.7 |
| c) | propylene | 9 | 180 | 70 | 63.9 |
| a) | octene-1 | 10 | 180 | 2 | 12.8 |
| b) | octene-1 | 10 | 180 | 2 | 25.3 |
| c) | octene-1 | 10 | 180 | 2 | 27.0 |

Note:
[+] The selectivity is based on converted olefin

What we claim is:

1. Process for the preparation of linear olefins having from 6 to 24 carbon atoms in the molecule, characterized by the introduction of one or more linear olefins having from 3 to 12 carbon atoms in the molecule to the catalysts obtained by activating, by means of an organic or inorganic base, a natural or synthetic crystalline zeolite on which has previously been deposited by ion exchange at least one metal chosen from among those belonging to group VIII of the periodic system of elements in an amount of from 0.1% to 50% by weight with respect to the zeolite, bringing the resulting product into contact with an organic or inorganic base in the liquid or gaseous form at a temperature in the range from −35 to 250° C for a time of at least 30 min, eliminating the excess of the base and heat-treating at temperatures in the range from 50 to 450° C for at least 30 min., and by operating at temperatures of from 130° to 260° C and at pressures of from 2 to 70 atmospheres.

2. Process in accordance with claim 1, characterized in that the zeolite has a pore diameter of from 8 to 13 A.

3. Process in accordance with claim 1, wherein the metal of group VIII of the periodic system is nickel or cobalt.

4. Process in accordance with claim 1, characterized in that a quantity of metal of from 1 to 20% by weight with respect to the zeolite itself is deposited on the zeolite.

5. Process in accordance with claim 1, characterized in that ammonia is used as an inorganic base.

6. Process in accordance with claim 1, characterized in that among the organic bases aliphatic amines such as monomethylamine, diethylamine, butylamine, and ethylenediamine and aromatic bases such as pyridine, piperidine, picoline, quinoline, and isoquinoline are used.

7. Process in accordance with claim 1, characterized in that the treatment with the base is carried out for times of from 3 to 5 hours.

8. Process in accordance with claim 1, characterized in that the excess of the base is eliminated at temperatures of below 250° C.

9. Process in accordance with claim 1, characterized in that the heat treatment is carried out at temperatures of from 150° to 350° C for a time of from 1 to 3 hours.

10. The process of claim 1 wherein said group VIII metal is selected from the group consisting of iron, cobalt, nickel, ruthenium, rhodium, palladium, osmium, iridium, and platinum; said zeolite has a specific surface area of from 200 to 1200 m$^2$/g and a pore diameter of from 6 to 15 A and contains silicon, aluminium and oxygen and one or more elements belonging to the alkali or alkaline earth metals; and said base is selected from the group consisting of monoethylamine, diethylamine, butylamine, ethylenediamine, pyridine, piperidine, picoline, quinoline, isoquinoline and ammonia.

11. Process in accordance with claim 8, wherein said temperature is between zero and 100° C.

12. Process in accordance with claim 8, whereby the elimination takes place in a stream of inert gas.

* * * * *